United States Patent
Hamandi

(10) Patent No.: US 9,610,590 B2
(45) Date of Patent: Apr. 4, 2017

(54) CENTRIFUGAL SEPARATING ASSEMBLY WITH A CONTAINER BODY HAVING A COMMON INLET-OUTLET PORT

(71) Applicant: Ziad Hamandi, Lake Worth, FL (US)

(72) Inventor: Ziad Hamandi, Lake Worth, FL (US)

( * ) Notice: Subject to any disclaimer, the term of this patent is extended or adjusted under 35 U.S.C. 154(b) by 242 days.

(21) Appl. No.: 14/159,689

(22) Filed: Jan. 21, 2014

(65) Prior Publication Data

US 2014/0206521 A1    Jul. 24, 2014

Related U.S. Application Data

(60) Provisional application No. 61/754,207, filed on Jan. 18, 2013.

(51) Int. Cl.

| | |
|---|---|
| *A61M 1/36* | (2006.01) |
| *B04B 5/04* | (2006.01) |
| *G01N 33/49* | (2006.01) |
| *B01L 3/00* | (2006.01) |

(52) U.S. Cl.
CPC ......... *B04B 5/0407* (2013.01); *A61M 1/3693* (2013.01); *B01L 3/502* (2013.01); *B01L 3/5021* (2013.01); *B04B 5/0421* (2013.01); *G01N 33/491* (2013.01); *B01L 2300/0854* (2013.01); *B01L 2400/0409* (2013.01)

(58) Field of Classification Search
CPC .. A61M 1/3693; B04B 5/0407; B04B 5/0421; G01N 33/491; B01L 3/5021; B01L 3/502; B01L 2300/0854; B01L 2400/0409
USPC ...................................................... 494/16, 37
See application file for complete search history.

(56) References Cited

U.S. PATENT DOCUMENTS

| | | | | |
|---|---|---|---|---|
| 4,861,477 | A * | 8/1989 | Kimura | B01L 3/5021 210/359 |
| 6,401,552 | B1 * | 6/2002 | Elkins | B01L 3/5021 422/548 |
| 9,329,165 | B2 * | 5/2016 | Ihm | G01N 33/491 |
| 2004/0067536 | A1 * | 4/2004 | Haubert | B01L 3/50215 435/7.2 |
| 2009/0289014 | A1 * | 11/2009 | Hoeppner | A61M 1/3693 210/741 |
| 2012/0251411 | A1 * | 10/2012 | Jeon | B01L 3/5021 422/533 |

(Continued)

FOREIGN PATENT DOCUMENTS

| | | | | |
|---|---|---|---|---|
| WO | WO 2004031770 A1 * | 4/2004 | | B01L 3/50215 |
| WO | WO 2011071353 A2 * | 6/2011 | | B01L 3/5021 |

*Primary Examiner* — Charles Cooley
*Assistant Examiner* — Shuyi S Liu
(74) *Attorney, Agent, or Firm* — The Concept Law Group, P.A.; Scott D. Smiley; Yongae Jun

(57) ABSTRACT

A centrifugal separating assembly for separating a fluid biological product into discrete components by centrifugation is disclosed. The assembly includes a first container defining a first cavity adapted to receive a human biological product, the first container having a circular upper wall, a cylindrical sidewall, and a concave shaped bottom wall. The assembly further includes a second container defining a second cavity adapted to receive discrete components, the second container having a convex shaped upper wall, a second cylindrical wall, and a circular bottom wall; and a tubular conduit providing fluid communication between the first cavity and the second cavity.

12 Claims, 4 Drawing Sheets

(56) References Cited

U.S. PATENT DOCUMENTS

| | | | |
|---|---|---|---|
| 2014/0349828 A1* | 11/2014 | U'Ren | B01L 3/50215 494/37 |
| 2014/0356254 A1* | 12/2014 | Lee | B01L 3/5021 422/548 |
| 2015/0104824 A1* | 4/2015 | Walker | B01L 3/5021 435/30 |

* cited by examiner

CENTRIFUGAL SEPARATING ASSEMBLY WITH A CONTAINER BODY HAVING A COMMON INLET-OUTLET PORT

CROSS-REFERENCE TO RELATED APPLICATION

This application claims priority to U.S. Provisional Patent Application No. 61/754,207 filed Jan. 18, 2013, the entirety of which is incorporated by reference.

FIELD OF THE INVENTION

The present invention relates generally to a centrifugal separating assembly, and more particularly relates to a centrifugal separating assembly having a first container coupled to a second container, the assembly configured such that heavier particulates travel from the first to the second container when the assembly is rotated in a centrifugal movement.

BACKGROUND OF THE INVENTION

It is sometimes desirable to separate particulates from a solution. It is well-known to use a centrifuge to separate particulates from a solution. As known in the art, a centrifuge is a device driven by a motor that rotates an object about a fixed axis, applying a centrifugal force perpendicular to the axis of rotation to separate an initial solution, or fluid product into discrete components.

Blood is a biological fluid product that can be characterized as a suspension of particles in a fluid. Blood primarily includes plasma, white wells, platelets, red blood cells, and other particulates present in different ratios and having different densities. When a blood sample is centrifuged, discrete layers are formed according to their densities. The least dense particulates will separate to form a top layer and the most dense particulates will separate and form a bottom layer. After blood is centrifuged a top layer is formed that is substantially plasma, a bottom layer is formed that is substantially red blood cells, and a middle layer is formed that is known in the art as a "buffy coat." The buffy coat contains white blood cells and platelets with an amount of plasma and red blood cells. It is often desirable to isolate the buffy coat for various applications.

It is sometimes desirable to adjust the ratio of red blood cells present in the buffy coat. However, many prior art devices are configured such that adjusting the ratio of red blood cells in the buffy coat requires several steps and is cumbersome to achieve. Also, many prior art devices are configured such that particulate residue builds on the sidewalls over time, reducing optimization of a desired concentrate.

Therefore, a need exists to overcome the problems with the prior art as discussed above and that reduces residue build-up on the sidewalls, optimizes the concentrate of a desired layer(s), increases fluid exchange efficiency, and provides a more convenient device and method of adjusting ratios of particulates in a desired layer.

SUMMARY OF THE INVENTION

The invention provides a centrifugal separating assembly that overcomes the hereinafore-mentioned disadvantages of the heretofore-known devices and methods of this general type and that separates fluid products into discrete components.

With the foregoing and other objects in view, there is provided, in accordance with the invention, a centrifugal separating assembly for separating a fluid biological product into discrete components by centrifugation, the assembly comprising:

a first container defining a first cavity adapted to receive and hold the fluid biological product, the first container having:
  a circular upper wall,
  a first cylindrical wall extending downwardly from a circumferential edge of the circular upper wall, and
  a concave shaped bottom wall extending inwardly and downwardly from a circumferential edge of the first cylindrical wall, the concave shaped bottom wall terminating at a distal end of the first container and the distal end of the first container defining a first tubular conduit receiving aperture;

a second container defining a second cavity adapted to receive discrete components of the fluid biological product during centrifugation, the second container having:
  a convex shaped upper wall extending upwardly and inwardly from an upper circumferential edge of a second cylindrical wall and terminating at a distal end of the second container, the distal end of the second container defining a second tubular conduit receiving aperture,
  the second cylindrical wall extending downwardly from a circumferential edge of the convex shaped upper wall, and
  a circular bottom wall extending inwardly from a lower circumferential edge of the second cylindrical wall; and a tubular conduit having a first linear length between a first distal end and a second distal end of the tubular conduit, the first and second distal ends being engaged with the first and the second tubular conduit receiving apertures, respectively, defining a fluid impermeable passageway between the first and the second container.

In accordance with another feature, the first container and the second container are made of polycarbonate.

In accordance with a further feature of the present invention, a volume of the second container is adapted to be a predetermined percentage of a volume of the first container.

In accordance with a further feature of the present invention, the second container is removeably attached to the tubular conduit.

In accordance with the present invention, an embodiment of the present invention also includes at least one of a self-sealing port and a valve disposed along the first linear length of the tubular conduit.

In accordance with another feature, an embodiment of the present invention also includes a third container adapted to engage a second linear length of the tubular conduit, the second linear length being substantially perpendicular to the first linear length.

In accordance with yet another feature, the assembly is adapted to rotate in a centrifugal movement where the first container is closest to an imaginary axis of rotation and the second container is distally located along an imaginary pendulum swing arm with reference to the second container, such that the second container will travel a further distance than will the first container during the centrifugal movement.

In accordance with a further feature of the present invention, the fluid biological product is human blood and the second container is sized to hold a volume equal to an anticipated percentage of red blood cells present in the blood within the first container.

In another embodiment of the present invention, there is provided a centrifugal separating assembly for separating a fluid biological product into discrete components, the assembly comprising:

a unitary container body defining a first cavity in fluid communication with a second cavity via a common inlet-outlet port, the unitary container body including:
  a concave shaped bottom wall extending downwardly from the first tubular sidewall, the concave shaped bottom wall defining an interior surface of the second cavity,
  a first tubular sidewall extending downwardly from an upper rim of the unitary container body, the first tubular sidewall defining an exterior surface of the unitary container body and the upper rim circumscribing an opening of the unitary container body, and
  a second tubular sidewall extending downwardly from the upper rim and terminating at the common inlet-outlet port, the second tubular sidewall defining an interior surface of the first cavity; and
a cap adapted to fittingly engage the upper rim to form a seal therewith and cover the opening of the unitary container body.

In accordance with a feature of the present invention, the assembly further includes an entry port formed in the cap, the entry port adapted to introduce the fluid biological product into the first cavity; and an exit port formed in the cap, the first exit port adapted to allow removal of discrete components from the first cavity.

In accordance with a further feature of the present invention, the assembly includes an exit port formed in the concave shaped bottom wall, the exit port adapted to allow removal of discrete components from the second cavity.

In accordance with a further feature of the present invention, the unitary container body includes polycarbonate.

In accordance with a further feature of the present invention, the second tubular sidewall is conical shaped.

In accordance with a further feature of the present invention, the first tubular sidewall is concentric with the second tubular sidewall and the second tubular sidewall has a smaller diameter than a diameter of the first tubular sidewall.

In accordance with a further feature of the present invention, the assembly further includes a convex shaped intermediate wall extending inwardly from a peripheral bottom edge of the first tubular sidewall, the convex shaped intermediate wall forming an arched roof of the second cavity, and wherein the common inlet-outlet port is integral with a bottom end of the second tubular sidewall and a central portion of the convex shaped intermediate wall.

In accordance with a further feature of the present invention, the common port is disposed within an interior of the unitary container body and between the first cavity and the second cavity. In accordance with a further feature of the present invention, yet another embodiment of the present invention includes a method of separating a fluid biological product into discrete layers by centrifugation, where the method includes providing a centrifugal separating assembly including a container body defining a first cavity in fluid communication with a second cavity via a common port; introducing the fluid biological product into an entry port of the first cavity; and after introducing the fluid biological product, centrifuging the fluid biological product for a predetermined amount of time to separate the fluid biological product into discrete layers such that a first discrete layer and a second discrete layer formed beneath the first discrete layer remains in the first cavity and a third discrete layer is formed in the second cavity.

In accordance with a further feature of the present invention, the method further includes after centrifuging the fluid biological product, removing the first discrete layer from the first cavity via an exit port; and after removing the first discrete layer from the first cavity, removing the second discrete layer from the first cavity via the exit port.

In accordance with a further feature of the present invention, the method further includes adjusting component ratios of the second discrete layer by, after centrifuging, removing an amount of the third discrete layer from the second cavity via a second exit port and, after removing the amount of the third discrete layer, centrifuging the fluid biological product again.

In accordance with a further feature of the present invention, the first, second, and third discrete layers are a plasma layer, a buffy coat layer, and a red blood cell layer, respectively.

Although the invention is illustrated and described herein as embodied in a centrifugal separating assembly, it is, nevertheless, not intended to be limited to the details shown because various modifications and structural changes may be made therein without departing from the spirit of the invention and within the scope and range of equivalents of the claims. Additionally, well-known elements of exemplary embodiments of the invention will not be described in detail or will be omitted so as not to obscure the relevant details of the invention.

Other features that are considered as characteristic for the invention are set forth in the appended claims. As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one of ordinary skill in the art to variously employ the present invention in virtually any appropriately detailed structure. Further, the terms and phrases used herein are not intended to be limiting; but rather, to provide an understandable description of the invention. While the specification concludes with claims defining the features of the invention that are regarded as novel, it is believed that the invention will be better understood from a consideration of the following description in conjunction with the drawing figures, in which like reference numerals are carried forward. The figures of the drawings are not drawn to scale.

Before the present invention is disclosed and described, it is to be understood that the terminology used herein is for the purpose of describing particular embodiments only and is not intended to be limiting. The terms "a" or "an," as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The term "coupled," as used herein, is defined as connected, although not necessarily directly, and not necessarily mechanically.

As used herein, the terms "about" or "approximately" apply to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure.

BRIEF DESCRIPTION OF THE DRAWINGS

The accompanying figures, where like reference numerals refer to identical or functionally similar elements throughout the separate views and which together with the detailed description below are incorporated in and form part of the specification, serve to further illustrate various embodiments and explain various principles and advantages all in accordance with the present invention.

DETAILED DESCRIPTION

Figure 1:
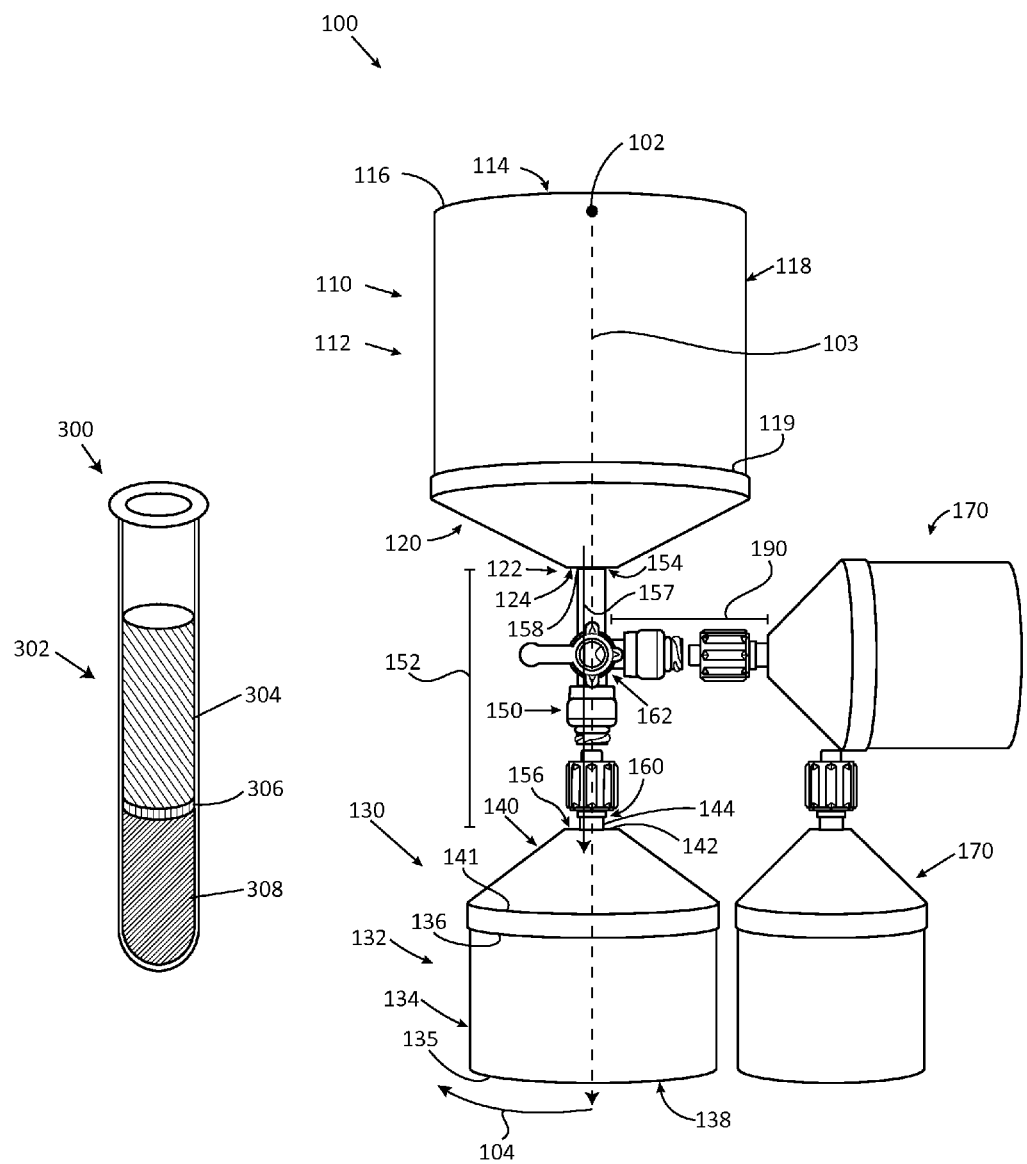
FIG. 1 is an elevation view of a first exemplary embodiment of a centrifuge separating assembly of the present invention.

While the specification concludes with claims defining the features of the invention that are regarded as novel, it is believed that the invention will be better understood from a consideration of the following description in conjunction with the drawing figures, in which like reference numerals are carried forward. It is to be understood that the disclosed embodiments are merely exemplary of the invention, which can be embodied in various forms.

The present invention provides a novel and efficient method and device for separating particulates from a solution. Embodiments of the invention provide a centrifugal separating assembly including a first container and a second container coupled via a tubular conduit, the assembly adapted to separate particulates of different densities (or weights) into discrete layers by centrifugation. In addition, embodiments of the invention provide an integral unitary container having a first cavity and a second cavity coupled via a common port and including a multitude of entry and exit ports formed on an external surface of the integral unitary container.

Referring now to FIG. 1, one embodiment of the present invention is shown in an elevation view. FIG. 1 shows several advantageous features of the present invention, but, as will be described below, the invention can be provided in several shapes, sizes, combinations of features and components, and varying numbers and functions of the components. The first example of a centrifugal separating assembly 100, as shown in FIG. 1, includes a first container 110, a second container 130, and a tubular conduit 150 providing fluid communication between the first container 110 and the second container 130, the assembly 100 adapted to channel fluid and particles into a direction during centrifugation to separate particles into discrete layers according to weight and density.

The first container 110 is configured as a storage vessel defining a volumetric space therein capable of holding a defined volume of fluid. The first container 110 includes a circular upper wall 114, a first cylindrical sidewall 118, and a concave shaped bottom wall 120, which, in combination, define a first cavity 112. The first cavity 112 is adapted to receive and store fluid biological product 302, such as blood. The circular upper wall 114 provides a planar surface that covers an upper end of the container 110 to seal fluid therein. The circular upper wall 114 preferably includes an entry port (not illustrated) for injecting fluid into the first cavity 112. The entry port is preferably a needleless self-sealing injection port. The first cylindrical sidewall 118 extends downwardly from a circumferential edge 116 of the circular upper wall 114. The first cylindrical sidewall 118 is bounded between the circular upper wall 114 and the concave shaped bottom wall 120. The concave shaped bottom wall 120 extends inwardly and downwardly from a lower circumferential edge 119 of the first cylindrical sidewall 118. The concave shaped bottom wall 120 terminates at a distal end 122 of the first container 110, the distal end 122 of the first container 110 defining a first tubular conduit receiving aperture 124. The first tubular conduit receiving aperture 124 is configured as a female attachment member and is adapted to mate with a distal end of the tubular conduit 140 for channeling fluid particles to the second container 140 during centrifugation.

The second container 130 is configured as a storage vessel defining a volumetric space therein capable of holding a defined volume of fluid. The second container 130 includes a convex shaped upper wall 140, a second cylindrical sidewall 134, and a circular bottom wall 138, which, in combination, define a second cavity 132 of the inventive assembly 100. The second cavity 132 is adapted to receive and store a predetermined volume of a separated, discrete layer of heavier fluid particles, such as the red blood cell layer 308, after centrifugation. The convex shaped upper wall 140 extends upwardly and inwardly from an upper circumferential edge 136 of the second cylindrical wall 134 and terminates at a distal end 142 of the second container 130, the distal end 142 of the second container 130 defining a second tubular conduit receiving aperture 144. The second tubular conduit receiving aperture 144 is configured as a female attachment member and is adapted to mate with a second, opposing distal end of the tubular conduit 150 for channeling fluid particles into the second container 130. The second cylindrical sidewall 134 extends downwardly from a circumferential edge 141 of the convex shaped upper wall 140. The second cylindrical sidewall 134 is bounded between the convex shaped upper wall 140 and the circular bottom wall 138. The circular bottom wall 138 extends inwardly from a lower circumferential edge 135 of the second cylindrical sidewall 134. The circular bottom wall 138 provides a planar support surface for containing and supporting the separated, discrete layer of heavier fluid particles.

As shown in FIG. 1, the second container 130 can be shaped similar to the first container 110, except that the volumetric storage space provided by the second container 130 can be different than the volumetric space provided by the first container 110. The orientation of the first and second container 110, 130 with respect to the tubular conduit 150 is opposite, as seen in FIG. 1. The first and second containers 110, 130 are preferably made of a polycarbonate material. The inventor of the present invention has discovered that particles do not tend to stick to container walls made of polycarbonate, thus, residue build-up on the interior surface of the containers 110, 130 is reduced and, advantageously, the concentrate of the discrete layers is optimized. In other embodiments, the containers 110 and 130 can include another transparent material, such as glass, or other polymer materials, such as polyethylene, polypropylene, silicone, plastic, and the like.

The walls 114, 118, and 120 of the first container 110 and the walls 140, 134, and 138 of the second container 130 can be integrated such that the first container 110 is formed as a unitary body and the second container 130 is formed as a unitary body. Alternatively, the walls 114, 118, and 120 and the walls 140, 134, and 138 can be fabricated as separate components that are subsequently, removeably attached together. As an example, the circular upper wall 114 and the first cylindrical sidewall 118 can be formed as an integral component, forming a cup member, with the concave shaped bottom wall 120, removeably attached thereto. Although the walls of the containers described herein above 114, 118, 120 and 140, 134, 138 are described as having a particular shape and configuration, it is understood that the description is exemplary and that the container walls described above can be in other shapes and configurations, as well, provided they allow fluid particles to be separated during centrifugation in accordance with the present invention. For example, the bottom wall 120 can be provided resembling a conical shape.

Advantageously, the present invention selects the volume of the containers 110, 130 based on anticipated percentage or ratios of ingredients of the fluid 302. As an example, approximately 40% of human blood is red blood cells 308. Therefore, the second container 130 of the inventive assembly 100 in FIG. 1 is adapted to hold a volume that is approximately 40% of the volume of the first container 110. As the assembly 100 is spun in a centrifugal manner, the heavier red blood cells 308 will force their way toward the distal end 122 of the first container 110, through the tubular conduit 150, and into the bottom of the second container 130 until the second container 130 is entirely or substantially full of red blood cells 308. The second container 130 can then be removed and its contents, i.e. red blood cells 308 in this example, can be utilized, as desired.

The tubular conduit 150 extends, linearly, a length 152 between a first distal end 154 and a second distal end 156 of the tubular conduit 150. The first and second distal ends 154 and 156 are engaged with the first and second tubular conduit receiving apertures 124 and 144, respectively, defining a fluid passageway 157 between the first and second container 110 and 130, which fluid passageway 157 is fluid impermeable and provides fluid communication between the first and second containers 110 and 130. When the first distal end 154 is engaged with the first tubular conduit receiving aperture 124, a first fluid-impermeable seal 158 is formed. Likewise, when the second distal end 156 is engaged with the second tubular conduit receiving aperture 144, a second fluid-impermeable seal 160 is formed. The tubular conduit 150 can be any length and diameter, but is preferably a length and diameter that optimizes fluid flow. A valve 162 can be provided at a point along the length 152 of the tubular conduit 150. In another embodiment, the valve 162 can preferably be replaced with a self-sealing port.

In an alternative embodiment, a third container 170 is provided. The third container 170 can be substantially the same as the second container 130, thus a description of the structure of the third container 170 is not provided, for brevity. The only substantial difference between the third container 170 and the second container 130 is the third container 170 is preferably sized to contain a volume equal to the anticipated percentage of a middle layer 306 anticipated to result from centrifugation. The third container 170 can be adapted to engage a second linear length 190 of the tubular conduit 150, with the second linear length 190 being substantially perpendicular to the first length 152 of the tubular conduit 150, as illustrated in FIG. 1.

When in use, a user places the centrifugal separating assembly 100 in a centrifuge. The assembly 100 is rotated in a centrifugal movement where the first container 110 is closest to an imaginary axis of rotation 102 and the second container 130 is distally located along an imaginary pendulum swing arm 103 with reference to the first container 110. In other words, during a centrifugal movement, the second container 130 will travel a further distance than will the first container 110. This rotation movement is represented by line 104 in FIG. 1. Heavier components of the fluid product 302 within the first container 110 will be pulled by a centrifugal force, through the tubular conduit 150, and into the second container 130. The molecularly heavier weighing ingredients will naturally be pulled closer to the bottom of the second container 130, i.e. further away from the first container 110 than the other less-heavy discrete components. Therefore, the first and second containers 110, 130 will have a separation of discrete components similar to what is shown in the test tube 300 in FIG. 1.

More specifically, if the fluid product 302 was human blood, after one centrifugation spin cycle, a majority of the heavier red blood cells 308 would be forced into the second container 130. The second container 130 is preferably sized to hold the anticipated percentage of red blood cells 308 (e.g. 40%). At the same time, the lighter plasma layer 304 and the buffy coat layer 306 are separated, but remain in the first container 110. Subsequently, the second container 130 can be swapped out for the third container 170 at the second distal end 156 of the tubular conduit 150. Next, the user initiates another centrifugation spin cycle. After the second centrifugation spin cycle, the buffy coat layer 306 is forced into the third container 170. The third container 170 is preferably sized to hold the anticipated percentage of the buffy coat layer 306 (e.g. 10%). Thus, after two spin cycles, each layer is separated and contained within a distinct container, ready for a desired use.

In the alternative embodiment, the third container 170 is already attached at the second linear length 190 of the tubular conduit 150, eliminating the additional step of swapping out the second and third containers 130, 170. Accordingly, during the second centrifugation spin cycle, the second container 130 is filled to capacity; therefore, the excess buffy coat layer 306 will naturally be forced into the third container 170.

Figure 2:
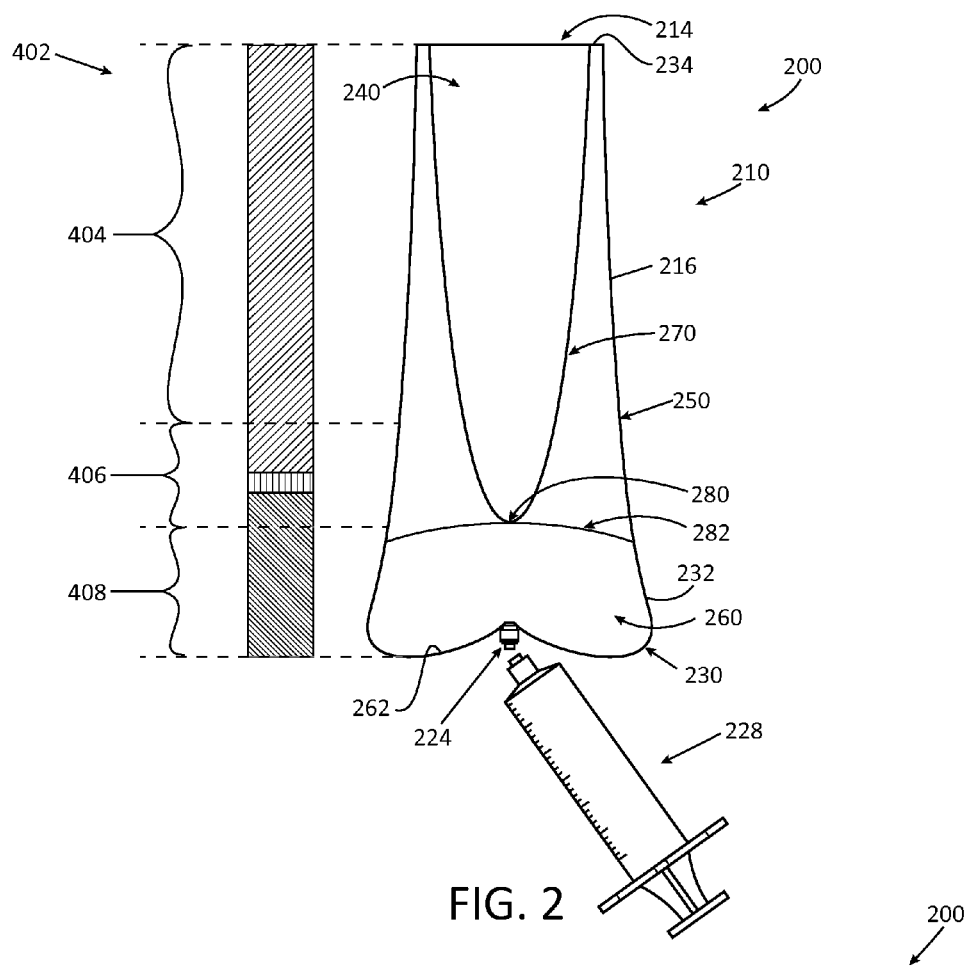
FIG. 2 is a schematic side elevation view of a second exemplary embodiment of a centrifuge separating assembly of the present invention.
Figure 3:
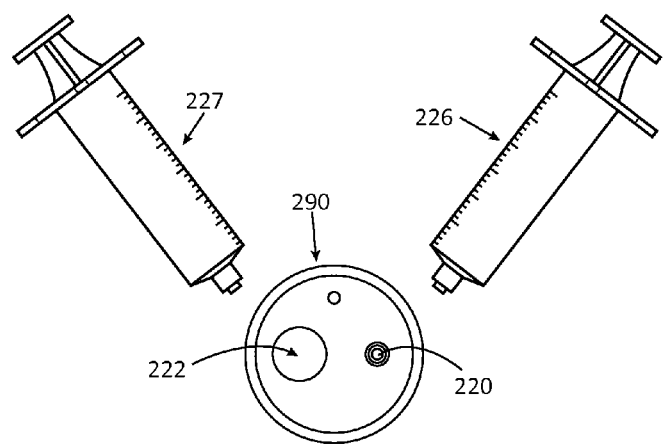
FIG. 3 is a top plan view of a cap of the centrifuge separating assembly originally introduced in FIG. 2.
Figure 4:
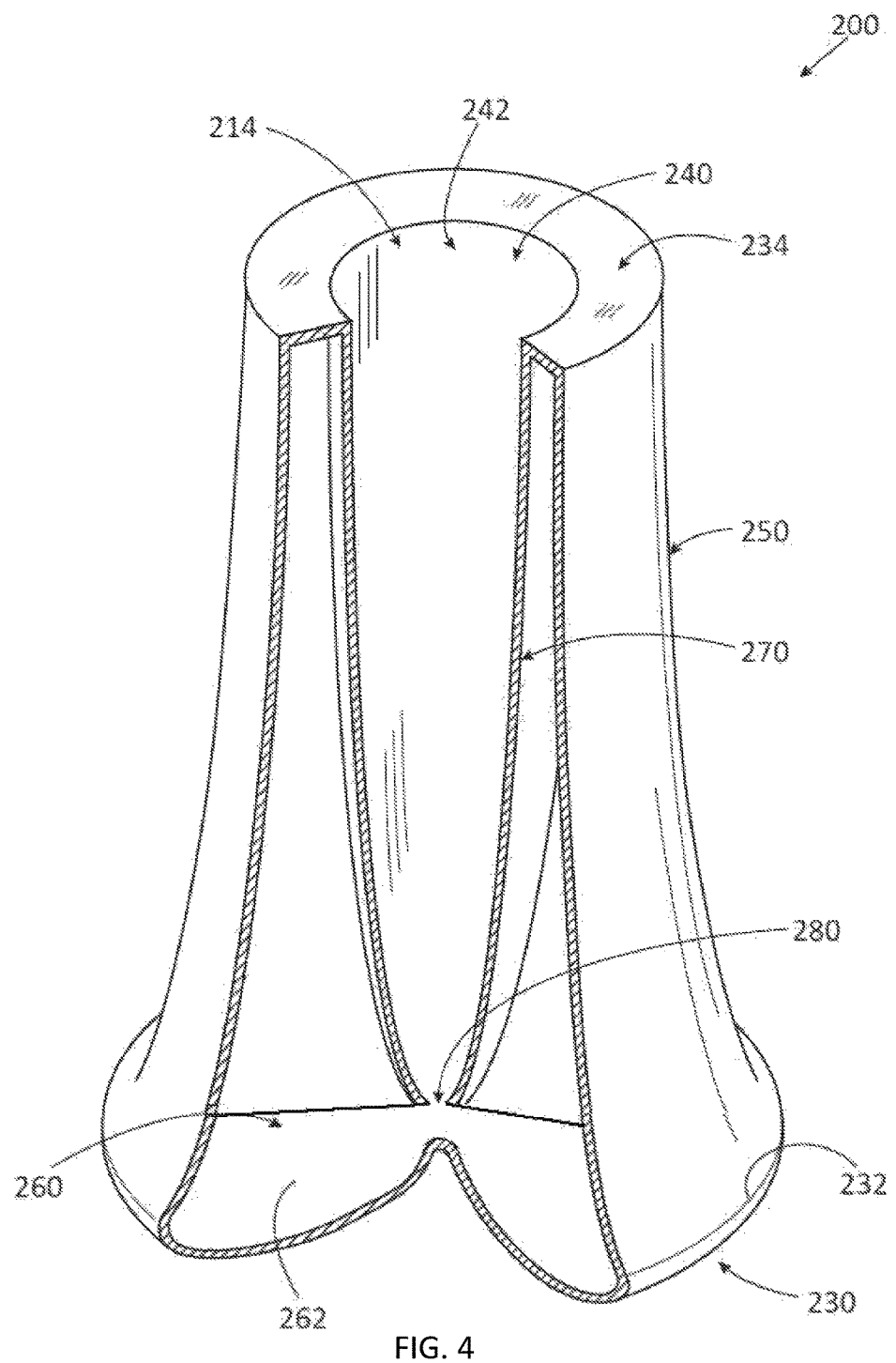
FIG. 4 is a perspective view of the centrifuge separating assembly originally introduced in FIG. 2.

Referring now to FIGS. 2-4, yet another alternative embodiment is illustrated. Another exemplary centrifugal separating assembly 200, as shown in FIGS. 2-4, includes a unitary container body 210, in which a first and a second container are integral, and a cap 290 adapted to seal the container body 210.

The unitary container body 210 defines a first cavity 240 in fluid communication with a second cavity 260 via a common inlet-outlet port 280. The unitary container body 210 may be manufactured using any of the well-known manufacturing processes known by those skilled in the art, including injection molding, vacuum forming, machining, and the like. The unitary container body 210 includes a concave shaped bottom wall 230, a convex shaped intermediate wall 282, a first tubular sidewall 250, and a second tubular sidewall 270.

The first tubular sidewall 250 extends downwardly from an upper rim 234 of the unitary container body 210, the first tubular sidewall 250 defining an exterior surface 216 of the unitary container body 210. The upper rim 234 circumscribes an opening 214 of the unitary container body 210. The first tubular sidewall 250 transitions into the concave shaped bottom wall 230.

The concave shaped bottom wall 230 defines an interior support surface 262 of the second cavity 260 and defining a receiving section for receiving and storing a separated, discrete component layer. The concave shaped bottom wall 230 curves inward toward a center of the unitary container body 210 along a bottom peripheral edge 232 of the first tubular sidewall 250. A first exit port 224 is formed in the concave shaped bottom wall 230, preferably at the center where the bottom wall 230 curves inwards. The first exit port 224 is adapted to allow removal of discrete components from the second cavity 260, preferably with a needleless syringe 228.

The convex shaped intermediate wall 282 provides a curved surface within the interior of the unitary container body 210 that increases movement of lighter particles, or cells to rise into the first cavity 240. The convex shaped intermediate wall 282 extends inwardly from a peripheral bottom edge of the first tubular sidewall 250, forming an arched roof of the second cavity 260. The convex shaped intermediate wall 282, the concave shaped bottom wall 230, and a segment of the first tubular sidewall 250 disposed therebetween, defines the second cavity 260.

The second tubular sidewall 270 extends downwardly from the upper rim 234 and terminates at the common inlet-outlet port 280, the second tubular sidewall 270 defining an interior surface 242 of the first cavity 240. The second tubular sidewall 270 is preferably conical shaped and is preferably concentric with the first tubular sidewall 250, with the second tubular sidewall 270 having a smaller diameter than a diameter of the first tubular sidewall 250.

The common inlet-outlet port 280 is preferably formed integrally with a bottom end of the second tubular sidewall 270 and a central portion of the convex shaped intermediate wall 282. The common port 280 is disposed within the interior of the unitary container body 210, between the first and second cavities 240 and 260. The common port 280 can be a self-sealing port. As with the centrifugal separating assembly 100, the walls 230, 250, and 270 of the centrifugal separating assembly 200 are preferably made of polycarbonate to reduce residue build-up on the walls.

The cap 290 is adapted to fittingly engage the upper rim 234 of the unitary container body 210, forming a seal therewith and covering the opening 214. The cap 290 can be configured to selectively, releasably engage the upper rim 234, or the cap 290 can be formed integrally with the upper rim 234 of the unitary container body 210. The cap 290 can have a generally planar surface. An entry port 220 is formed in the cap 290, the entry port 220 adapted to introduce the fluid biological product 402 into the first cavity 240. The entry port 220 is preferably a needleless self-sealing injection port, configured to allow injection of fluids with a needleless syringe 226. A second exit port 222 can also be formed in the cap 290, the second exit port 222 adapted to allow discrete components from the first cavity 240 to be removed, preferably with a needleless syringe 227.

Figure 5:
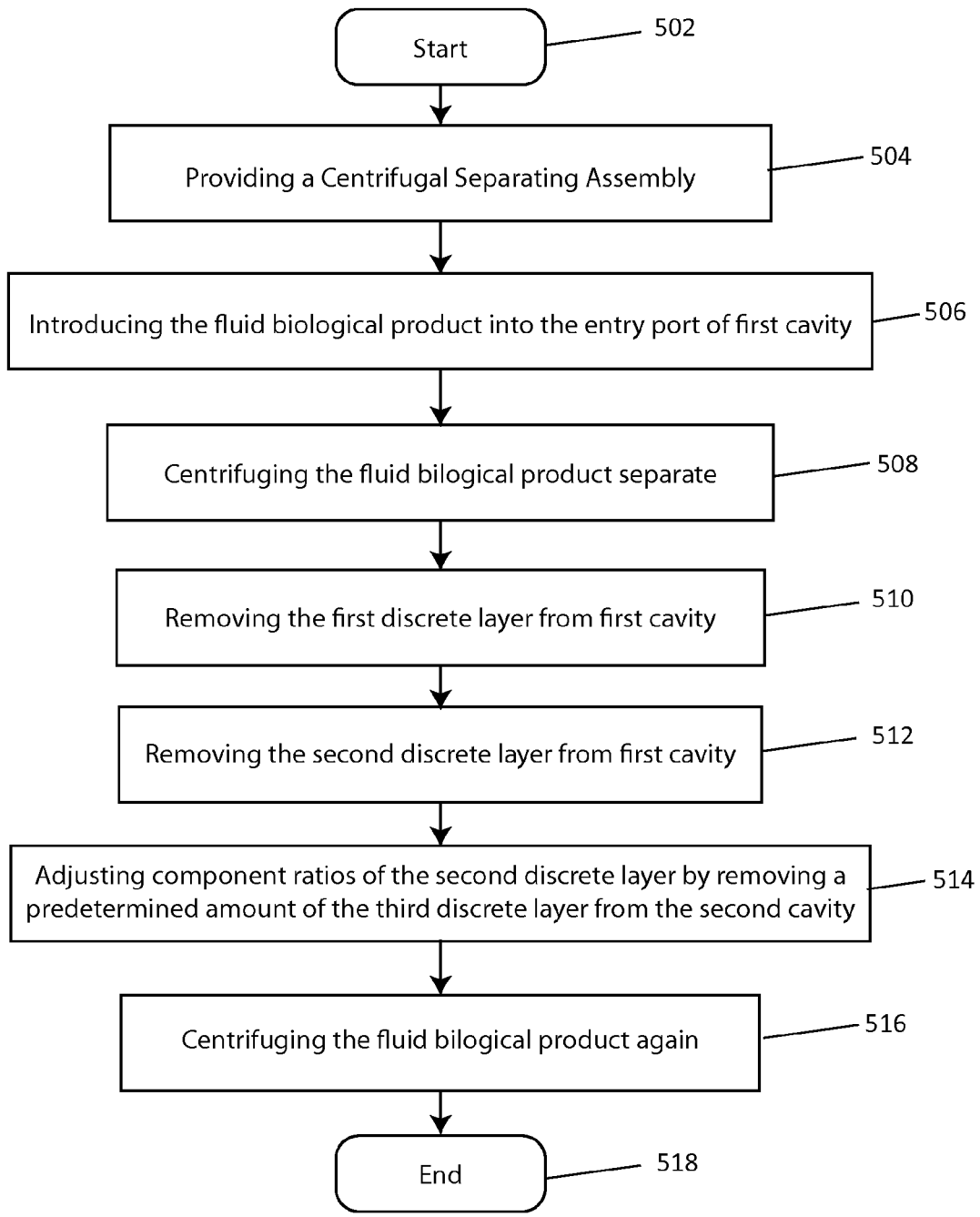
FIG. 5 is a flow diagram illustrating a process for using the centrifuge separating assembly originally introduced in FIG. 2.

Referring now primarily to FIGS. 5 and 2, the present invention provides a process for separating the fluid biological product 402 into first, second, and third discrete layers 404, 406, and 408. For illustrative purposes, the fluid biological product 402 is human blood and the discrete layers are a plasma layer 404, a buffy coat layer 406, and a red blood cell layer 408. The process begins at step 502 and continues immediately to step 504, where a user provides a centrifugal separating assembly, such as the centrifugal separating assembly 200 having a unitary container body 210 defining a first cavity 240 in fluid communication with a second cavity 260 via a common inlet-outlet port 280. In step 506, the user introduces the fluid biological product 402 into the entry port 220 of the first cavity 240. The user can use a needleless syringe 226 to inject human blood 402 into the entry port 220. After introducing the human blood 402, in step 508, the user can centrifuge the blood 402 for a predetermined amount of time and at a specific speed (g-force) to separate the blood 402 into discrete layers such that a first discrete layer 404 and a second discrete layer 406, formed immediately beneath the first discrete layer 404, remains in the first cavity 240 and a third discrete layer 408 is formed in the second cavity 260. The centrifuging forces separation of the components according to weight and forces the third discrete layer 408 to travel from the first cavity 240 into the second cavity 260. In step 510, after centrifuging the blood 402, the user removes the first discrete layer 404 from the first cavity 240 via the second exit port 222. The user can remove the first discrete layer 404 by extracting it with the syringe 227, which in one embodiment can be a depth-gauged syringe. Measurement markings can be provided on the surface of the second tubular sidewall 270 to guide the user as to the amount of fluid particles withdrawn from the first cavity 240. In step 512, after removing the first discrete layer 404 from the first cavity 240, the user removes the second discrete layer 406 from the first cavity 240. In many applications, the second, middle layer is the desired layer. Regarding human blood samples, the buffy coat 406 is desired for various advantageous applications.

In step 514, the user can adjust component ratios of the buffy coat 406 in the bottom of the first cavity 240 by, after centrifuging the blood sample 402 in step 508, removing a predetermined amount of the red blood cells 408 from the second cavity 260 and then, in step 516, the user can centrifuge the blood sample 402 again. This will force more red blood cells 408 into the second cavity 260, advantageously reducing the percentage of red blood cells 408 within the buffy coat 406 in the bottom of the first cavity 240. The user can repeat steps 514 and 516 until the desired component ratios of the buffy coat 406 are achieved. The process ends at step 518. Although the exemplary method discusses centrifugation of human blood, it is understood that that the fluid biological product can be other fluids, such as, for example, non-human blood, or bone marrow.

A centrifugal separating assembly has been disclosed that can be placed in a centrifuge to separate a fluid product into discrete components according to varying weights of the discrete components.

What is claimed is:

1. A centrifugal separating assembly for separating a fluid biological product into discrete components, the assembly comprising:
    a container body defining a first cavity in fluid communication with a second cavity via a common inlet-outlet port, the container body including:
        a first tubular sidewall extending downwardly from an upper rim of the container body, the first tubular sidewall defining an exterior surface of the container body and the upper rim circumscribing an opening of the container body,
        a concave shaped bottom wall extending downwardly from the first tubular sidewall, the concave shaped bottom wall defining an interior surface of the second cavity, and
        a second tubular sidewall extending downwardly from the upper rim and terminating at the common inlet-outlet port, the second tubular sidewall fixedly connected to the first tubular sidewall and defining an interior surface of the first cavity.

2. The centrifugal separating assembly according to claim 1, further comprising:
a cap adapted to fittingly engage the upper rim to form a seal therewith and cover the opening of the container body;
an entry port formed in the cap, the entry port adapted to introduce the fluid biological product into the first cavity; and
an exit port formed in the cap, the exit port adapted to allow removal of discrete components from the first cavity.

3. The centrifugal separating assembly according to claim 1, further comprising an exit port formed in the concave shaped bottom wall, the exit port adapted to allow removal of discrete components from the second cavity.

4. The centrifugal separating assembly according to claim 1, wherein the container body includes polycarbonate.

5. The centrifugal separating assembly according to claim 1, wherein the second tubular sidewall is conical shaped.

6. The centrifugal separating assembly according to claim 1, wherein the first tubular sidewall is concentric with the second tubular sidewall and the second tubular sidewall has a smaller diameter than a diameter of the first tubular sidewall.

7. The centrifugal separating assembly according to claim 1, further comprising a convex shaped intermediate wall extending inwardly from a peripheral bottom edge of the first tubular sidewall, the convex shaped intermediate wall forming an arched roof of the second cavity, and wherein the common inlet-outlet port is integral with a bottom end of the second tubular sidewall and a central portion of the convex shaped intermediate wall.

8. The centrifugal separating assembly according to claim 1, wherein the common inlet-outlet port is disposed within an interior of the container body and between the first cavity and the second cavity.

9. A method of separating a fluid biological product into discrete layers by centrifugation, the method comprising:
providing a centrifugal separating assembly including a container body defining a first cavity in fluid communication with a second cavity via a common port, the container body including:
a first tubular sidewall extending downwardly from an upper rim of the container body, the first tubular sidewall defining an exterior surface of the container body and the upper rim circumscribing an opening of the container body,
a concave shaped bottom wall extending downwardly from the first tubular sidewall, the concave shaped bottom wall defining an interior surface of the second cavity,
a second tubular sidewall extending downwardly from the upper rim and terminating at the common port, the second tubular sidewall fixedly connected to the first tubular sidewall and defining an interior surface of the first cavity;
introducing the fluid biological product into an entry port of the first cavity; and
after introducing the fluid biological product, centrifuging the fluid biological product for a predetermined amount of time to separate the fluid biological product into discrete layers such that a first discrete layer and a second discrete layer formed beneath the first discrete layer remains in the first cavity and a third discrete layer is formed in the second cavity.

10. The method of separating a fluid biological product into discrete layers by centrifugation according to claim 9, further comprising:
after centrifuging the fluid biological product, removing the first discrete layer from the first cavity via an exit port; and
after removing the first discrete layer from the first cavity, removing the second discrete layer from the first cavity via the exit port.

11. The method of separating a fluid biological product into discrete layers by centrifugation according to claim 9, further comprising adjusting component ratios of the second discrete layer by, after centrifuging, removing an amount of the third discrete layer from the second cavity via a second exit port and, after removing the amount of the third discrete layer, centrifuging the fluid biological product again.

12. The method of separating a fluid biological product into discrete layers by centrifugation according to claim 9, wherein the first, second, and third discrete layers are a plasma layer, a buffy coat layer, and a red blood cell layer, respectively.

* * * * *